:::

United States Patent
Oh et al.

(10) Patent No.: US 11,916,197 B2
(45) Date of Patent: Feb. 27, 2024

(54) ELECTROLYTE ADDITIVES FOR SECONDARY BATTERY, NON-AQUEOUS ELECTROLYTE FOR SECONDARY BATTERY COMPRISING SAME AND SECONDARY BATTERY

(71) Applicant: LG Energy Solution, Ltd., Seoul (KR)

(72) Inventors: Jeong Woo Oh, Daejeon (KR); Chul Haeng Lee, Daejeon (KR); Sung Guk Park, Daejeon (KR)

(73) Assignee: LG Energy Solution, Ltd. (KR)

(*) Notice: Subject to any disclaimer, the term of this patent is extended or adjusted under 35 U.S.C. 154(b) by 108 days.

(21) Appl. No.: 17/702,948

(22) Filed: Mar. 24, 2022

(65) Prior Publication Data
US 2022/0320583 A1    Oct. 6, 2022

(30) Foreign Application Priority Data
Mar. 31, 2021 (KR) .................. 10-2021-0042033

(51) Int. Cl.
*H01M 10/0567* (2010.01)
*H01M 10/0525* (2010.01)
*C07D 233/60* (2006.01)
*H01M 10/0569* (2010.01)
*H01M 10/0568* (2010.01)

(52) U.S. Cl.
CPC ...... *H01M 10/0567* (2013.01); *C07D 233/60* (2013.01); *H01M 10/0525* (2013.01); *H01M 10/0568* (2013.01); *H01M 10/0569* (2013.01)

(58) Field of Classification Search
None
See application file for complete search history.

(56) References Cited

U.S. PATENT DOCUMENTS

| | | |
|---|---|---|
| 2020/0044287 A1 | 2/2020 | Kim et al. |
| 2021/0328266 A1 | 10/2021 | Kim et al. |
| 2022/0115701 A1 | 4/2022 | An et al. |
| 2022/0131192 A1 | 4/2022 | Kim et al. |
| 2022/0223911 A1 | 7/2022 | Kim et al. |

FOREIGN PATENT DOCUMENTS

| | | | | |
|---|---|---|---|---|
| EP | 3879617 A1 | 9/2021 | | |
| EP | 3913719 A1 | 11/2021 | | |
| JP | 2007095983 A | 4/2007 | | |
| JP | 3911870 B2 | 5/2007 | | |
| JP | 2018145183 A | 9/2018 | | |
| KR | 20090080298 A | 7/2009 | | |
| KR | 101297786 B1 | 8/2013 | | |
| KR | 20160052658 A | 5/2016 | | |
| KR | 20190008100 A | 1/2019 | | |
| KR | 20200074902 A | 6/2020 | | |
| KR | 20200089623 A | 7/2020 | | |
| KR | 20200105227 A | 9/2020 | | |
| KR | 102179846 B1 | 11/2020 | | |
| KR | 20210023756 A | 3/2021 | | |
| KR | 20210041382 A | 4/2021 | | |
| WO | WO-2013137596 A1 * | 9/2013 | ........... | C07D 233/56 |
| WO | 2020149678 A1 | 7/2020 | | |
| WO | 2020153791 A1 | 7/2020 | | |

OTHER PUBLICATIONS

Fedeli, E. et al., "Synthesis and Use of Zwitterion Bearing Sulfonyl(trifluoromethane sylfonyl)imide Anion as Additive for Polymer Electrolytes," Applied Sciences, Oct. 2020, pp. 1-11.
Extended European Search Report for Application No. 22781440.7 dated Nov. 24, 2023, pp. 1-6.
Gaalova, J. et al: "Nafion membranes modified by cationic cyclodextrin derivatives for enantioselective separation", Separation and Purification Technology, Elsevier Science, Amsterdam, NL, vol. 266, Mar. 10, 2021 (Mar. 10, 2021), XP086549157.

* cited by examiner

Primary Examiner — Wyatt P McConnell
(74) Attorney, Agent, or Firm — Lerner David LLP

(57) ABSTRACT

An electrolyte solution additive for a secondary battery, a non-aqueous electrolyte solution including the same, and a lithium secondary battery including the same are disclosed herein. To be specific, the above non-aqueous electrolyte solution includes the electrolyte solution additive comprising the compound represented by Formula 1:

[Formula 1]

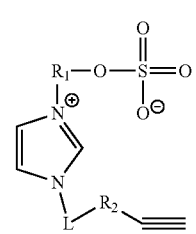

wherein, in Formula 1, $R_1$ and $R_2$ are each independently an unsubstituted or substituted alkylene group having 1 to 5 carbon atoms, and L is a direct bond, —O—, —COO—, —RO—, or —R'COO—, wherein R and R' are each independently an alkylene group having 1 to 10 carbon atoms. The additive has an excellent effect of scavenging a decomposition product generated from a lithium salt.

10 Claims, No Drawings

ELECTROLYTE ADDITIVES FOR SECONDARY BATTERY, NON-AQUEOUS ELECTROLYTE FOR SECONDARY BATTERY COMPRISING SAME AND SECONDARY BATTERY

CROSS-REFERENCE TO RELATED APPLICATIONS

This application claims priority form Korean Patent Application No. 10-2021-0042033, filed on Mar. 31, 2021, the disclosure of which is incorporated herein by reference.

BACKGROUND OF THE INVENTION

Field of the Invention

The present invention relates to an electrolyte solution additive for a secondary battery, and a non-aqueous electrolyte solution for a lithium secondary battery and a lithium secondary battery which include the same, and more particularly, to an electrolyte solution additive for a secondary battery which has an excellent effect of scavenging a decomposition product generated from a lithium salt, and a non-aqueous electrolyte solution for a lithium secondary battery and a lithium secondary battery which include the same.

Description of the Related Art

As dependence on electrical energy is gradually increasing in modern society, renewable energy generation, which may increase production without causing environmental problems, has emerged as a next-generation power generation system.

With respect to renewable energy, since it exhibits intermittent power generation characteristics, a large-capacity power storage device is indispensable to supply power stably. A lithium-ion battery is in the spotlight as a device exhibiting the highest energy density which is currently commercialized among power storage devices.

The lithium-ion battery is composed of a positive electrode formed of a transition metal oxide containing lithium, a negative electrode capable of storing the lithium, an electrolyte solution that includes a non-aqueous organic solvent containing a lithium salt, and a separator.

In the lithium-ion battery, $LiPF_6$ is mainly used as a representative lithium salt in order to achieve suitable characteristics of the battery. However, since the $LiPF_6$ is very vulnerable to heat, it generates a Lewis acid, such as $PF_5$, while being thermally decomposed when the battery is exposed to high temperatures. Such a Lewis acid material not only causes a decomposition reaction of the non-aqueous organic solvent such as ethylene carbonate, but also degrades a film, such as a solid electrolyte interphase (SEI), formed on a surface of the electrode to cause additional decomposition of the electrolyte solution, an increase in resistance, and dissolution of transition metal from the positive electrode.

Furthermore, dissolved transition metal ions become a cause of increasing resistance of the positive electrode while being re-deposited on the positive electrode, and, in contrast, the dissolved transition metal ions cause self-discharge of the negative electrode by being transferred to the negative electrode through the electrolyte solution and then electrodeposited on the negative electrode, and become a cause of increasing resistance and degrading lifetime due to additional consumption of lithium ions caused by destruction and regeneration of the solid electrolyte interphase (SEI).

Thus, in order to suppress a degradation behavior of the battery when the battery is exposed to high temperatures, there is a growing interest in a method capable of maintaining passivation ability of the SEI while scavenging byproducts such as HF and $PF_5$ formed by thermal decomposition of the lithium salt.

PRIOR ART DOCUMENT

[Patent Document]
(Patent Document 1) Japanese Patent Application Laid-open Publication No. 2018-0145183

SUMMARY OF THE INVENTION

An aspect of the present invention provides an electrolyte solution additive for a secondary battery which may scavenge a decomposition product generated from a lithium salt and may simultaneously achieve a solid electrolyte interphase (SEI) strengthening effect.

Another aspect of the present invention provides a non-aqueous electrolyte solution for a lithium secondary battery, which may achieve high-temperature stability and high-temperature cycle characteristics by including the electrolyte solution additive for a secondary battery, and a lithium secondary battery including the same.

According to an aspect of the present invention, there is provided an electrolyte solution additive for a secondary battery which includes a compound represented by Formula 1.

[Formula 1]

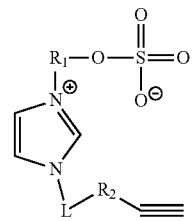

In Formula 1,
$R_1$ and $R_2$ are each independently an unsubstituted or substituted alkylene group having 1 to 5 carbon atoms, and
L is a direct bond, —O—, —COO—, —RO—, or —R'COO—, wherein R and R' are each independently an alkylene group having 1 to 10 carbon atoms.

According to another aspect of the present invention, there is provided a non-aqueous electrolyte solution for a lithium secondary battery which includes the electrolyte solution additive for a secondary battery.

According to another aspect of the present invention, there is provided a lithium secondary battery, comprising:
  a positive electrode including a positive electrode active material;
  a negative electrode including a negative electrode active material;
  a separator disposed between the negative electrode and the positive electrode; and
  the non-aqueous electrolyte solution for a lithium secondary battery of the present invention.

DETAILED DESCRIPTION OF THE PREFERRED EMBODIMENT

First, before describing the present invention, it will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

The terms used in the present specification are used to merely describe exemplary embodiments, but are not intended to limit the invention. The terms of a singular form may include plural forms unless referred to the contrary.

It will be further understood that the terms "include," "comprise," or "have" in this specification specify the presence of stated features, numbers, steps, elements, or combinations thereof, but do not preclude the presence or addition of one or more other features, numbers, steps, elements, or combinations thereof.

In the present specification, the expression denotes wt % unless explicitly stated otherwise.

Before describing the present invention, the expressions "a" and "b" in the description of "a to b carbon atoms" in the specification each denote the number of carbon atoms included in a specific functional group. That is, the functional group may include "a" to "b" carbon atoms.

Also, unless otherwise defined in the specification, the expression "substitution" denotes that at least one hydrogen bonded to carbon is substituted with an element other than hydrogen, for example, an alkyl group having 1 to 5 carbon atoms or a fluorine element.

In the present specification, a "difference in reduction potential versus lithium between additives" may be calculated using the following method.

For example, after $LiPF_6$ is dissolved in a non-aqueous organic solvent, in which ethylene carbonate (EC) and ethyl methyl carbonate (EMC) are mixed in a volume ratio of 30:70, such that a concentration of the $LiPF_6$ is 1.0 M, a non-aqueous electrolyte solution is prepared by adding 0.5 wt % of the electrolyte solution additive for a secondary battery of the present invention. Then, a negative electrode prepared by coating a negative electrode collector (Cu) with graphite, a porous polyethylene separator, and lithium metal (Li metal), as a positive electrode, are stacked, and the above-prepared non-aqueous electrolyte solution is injected to assemble a 2 Ah stack cell. Then, a differential capacity-voltage curve is obtained by differentiating a capacity-voltage curve during a constant current charging process which is obtained while charging the cell under a 0.1 C CC (constant current) condition, and a voltage, at which a reduction peak identified from the curve appears, is defined as a reduction potential of the electrolyte solution additive for a secondary battery of the present invention. Subsequently, after a cell is prepared in the same manner as above except that a non-aqueous electrolyte solution is prepared by including other additives instead of the electrolyte solution additive for a secondary battery of the present invention, a differential capacity-voltage curve is obtained, and a voltage, at which a reduction peak identified from the curve appears, is defined as a reduction potential of the other additives. Finally, other additives, in which an absolute value of a difference in reduction potential between the other additives and the electrolyte solution additive of the present invention was included in a range of 0.0 V to 2.2 V, was used as other additives in the present invention.

Hereinafter, the present invention will be described in more detail.

In general, with respect to a lithium secondary battery, high-temperature storage characteristics may be secured by forming a film having passivation ability on surfaces of a positive electrode and a negative electrode while a non-aqueous electrolyte solution is decomposed during initial charge and discharge. However, the film may be degraded by a Lewis acid material, such as HF and $PF_5$, formed by thermal decomposition of a lithium salt ($LiPF_6$, etc.) widely used in a lithium-ion battery. That is, since surface resistance of the electrode is increased due to a change in structure of the surface if dissolution of transition metal elements occurs from the positive electrode by attack of the Lewis acid material and theoretical capacity is reduced as the metallic elements, as redox centers, are lost, capacity may be reduced. Also, since transition metal ions thus dissolved are electrodeposited on the negative electrode reacting in a strong reduction potential range to not only consume electrons, but also destruct the film when electrodeposited to expose the surface of the negative electrode, an additional non-aqueous electrolyte solution decomposition reaction may be caused. As a result, capacity of a cell may be continuously reduced while resistance of the negative electrode and irreversible capacity are increased.

Thus, the present invention aims at providing an additive having excellent effects of scavenging a decomposition product generated from the lithium salt and strengthening a solid electrolyte interphase (SEI), and a non-aqueous electrolyte solution and a lithium secondary battery which include the same.

Electrolyte Solution Additive for Secondary Battery

In the present invention, provided is an electrolyte solution additive for a secondary battery which includes a compound represented by the following Formula 1.

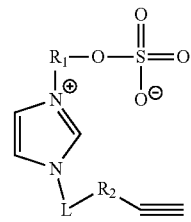

[Formula 1]

In Formula 1, $R_1$ and $R_2$ are each independently an unsubstituted or substituted alkylene group having 1 to 5 carbon atoms, and L is a direct bond, —O—, —COO—, —RO—, or —R'COO—, wherein R and R' are each independently an alkylene group having 1 to 10 carbon atoms.

Also, in Formula 1, $R_1$ and $R_2$ are each independently an unsubstituted or substituted alkylene group having 1 to 3 carbon atoms, and L is —O—, —COO—, or —R'COO—, wherein R' may be an alkylene group having 1 to 5 carbon atoms.

Furthermore, in Formula 1, L may be —O— or —COO—.

Specifically, the compound represented by Formula 1 may be at least one selected from compounds represented by Formula 1A or Formula 1B below.

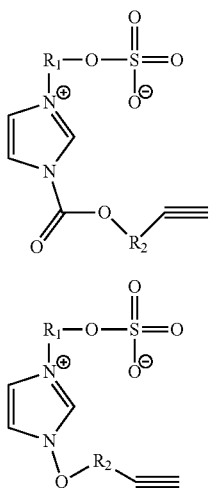

[Formula 1A]

[Formula 1B]

In Formula 1A or 1B, $R_1$ and $R_2$ are each independently an unsubstituted or substituted alkylene group having 1 to 5 carbon atoms.

Preferably, the compound represented by Formula 1 may be a compound represented by Formula 1A-1 or Formula 1B-1 below.

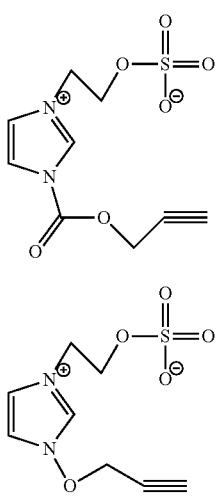

[Formula 1A-1]

[Formula 1B-1]

Particularly, since the compound represented by Formula 1A-1 includes a carbonate group in its structure, it has better Li ion transfer capability. Thus, the compound represented by Formula 1A-1 is more preferable than the compound represented by Formula 1B-1, in terms of further improving ionic conductivity of the non-aqueous electrolyte solution.

The compound represented by Formula 1 is a zwitterionic compound having both anionic and cationic moieties in one molecular structure, wherein, since a nitrogen atom of the cationic moiety acts as a Lewis base, it has a high binding force with the Lewis acid material generated as the decomposition product of the lithium salt. Thus, it may easily scavenge a by-product causing degradation of the secondary battery at high temperatures, for example, the decomposition product generated by the thermal decomposition of the lithium salt. In addition, a nitrogen (N) atom-based material may form a nitrogen (N) atom-based film (SEI) on the surface of the negative electrode while being electrochemically reductively decomposed. The nitrogen (N) atom-based film has a characteristic in which it is not easily decomposed and maintained when the battery is exposed to high temperatures. Thus, with respect to the non-aqueous electrolyte solution of the present invention including the compound represented by Formula 1, since the characteristic, in which the SEI is not decomposed and stably maintained on the surface of the negative electrode, is provided, a negative electrode reduction reaction of additional transition metals due to the decomposition of the SEI may be controlled and electrodeposition of the dissolved transition metal on the negative electrode during high-temperature storage may be prevented.

Also, since the compound represented by Formula 1 includes an easily-reducible propargyl functional group as a terminal group, it may form a passivation film with enhanced durability while being reductively decomposed on the surface of the negative electrode. That is, since a stable film may be formed at an interface between an electrolyte and the positive electrode and negative electrode, stability may be secured by suppressing a side reaction while using a high nickel positive electrode active material, and thus, it is effective in improving high-temperature durability and long lifetime as well as initial performance of the lithium secondary battery.

With respect to a nickel (Ni) element included in the positive electrode formed of a lithium composite metal oxide, it exists in the form of a stable nickel ion ($Ni^{2+}$) before charge and discharge, and changes into a $Ni^{3+}$ ion or $Ni^{4+}$ ion as an oxidation number increases after the charge and discharge. Unlike the stable $Ni^{2+}$ ion, a side reaction occurs in which the $Ni^{3+}$ ion or $Ni^{4+}$ ion is reduced to the $Ni^{2+}$ ion while rapid oxygen desorption occurs due to instability. Since the desorbed oxygen reacts with the electrolyte solution to change surface properties of the electrode or increase charge transfer impedance of the electrode surface to reduce capacity or high-rate capability, there is a problem in that energy density is reduced. This phenomenon is further intensified on a surface of a high-Ni positive electrode. Thus, it is very important to form a stable film capable of preventing a side reaction with the electrolyte solution on the surface of the high-Ni positive electrode during preparation of the secondary battery and providing surface stability. The compound represented by Formula 1, which is used as the electrolyte solution additive in the present invention, may form a stable film of a lithium-containing alkyl sulfonate type on the surfaces of the positive electrode and the negative electrode by binding with lithium ions contained in the lithium salt. Therefore, since it is possible to reduce the side reaction by preventing a contact of the desorbed oxygen or $Ni^{4+}$ ion with the electrolyte solution and to effectively suppress the dissolution of the transition metal from the positive electrode, the reduction in the capacity or high-rate capability of the secondary battery may be improved.

As described above, in a case in which the compound of Formula 1 is used as the additive, a more robust film may be formed on the surfaces of the positive electrode and the negative electrode, an effect of suppressing the dissolution of the transition metal from the positive electrode at high temperature may be further improved accordingly, and high-temperature storage and cycle performance may be improved by mitigating self-discharge of the secondary battery.

A sulfate group (SO$_4^-$), which is one of the terminal groups of the compound represented by Formula 1, is a substituent that is easily bonded to a hydrogen. Thus, a portion of the compound represented by Formula 1 may exist in the form of a compound represented by the following Formula 2 in the non-aqueous electrolyte solution.

[Formula 2]

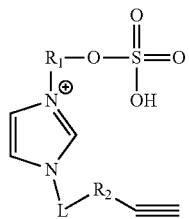

In Formula 2,

R$_1$, R$_2$, and L are as defined in Formula 1.

Non-Aqueous Electrolyte Solution

Also, a non-aqueous electrolyte solution according to an embodiment of the present invention includes the electrolyte solution additive including the compound represented by Formula 1.

The non-aqueous electrolyte solution may further include a lithium salt, an organic solvent, and optionally a compound, in which an absolute value of a difference in reduction potential versus lithium between the compound and the compound represented by Formula 1 is in a range of 0.0 V to 2.2 V, as other additives.

(1) Electrolyte Solution Additive for Secondary Battery

The non-aqueous electrolyte solution of the present invention includes the electrolyte solution additive for a secondary battery including the compound represented by Formula 1, and, since a description thereof overlaps with that described above, the description thereof will be omitted.

In consideration of an effect of forming a stable film on the surface of the electrode and an effect of scavenging a thermal decomposition product of the lithium salt, the electrolyte solution additive for a secondary battery may be present in an amount of 0.05 wt % to 5 wt % based on a total weight of the non-aqueous electrolyte solution.

If the amount of the electrolyte solution additive for a secondary battery included is within the above range, the dissolution of the transition metal of a positive electrode active material at high temperatures may be effectively suppressed by forming a robust film on the surface of the positive electrode while reducing disadvantages, such as the side reaction due to the additive, a reduction in capacity, and an increase in resistance, as much as possible, and excellent high-temperature durability may be achieved by effectively scavenging the thermal decomposition product of the lithium salt.

That is, if the amount of the electrolyte solution additive for a secondary battery is 0.05 wt % or more, the effect of scavenging the thermal decomposition product of the lithium salt may be maintained even if operation time is increased, and the effect of suppressing the dissolution of the transition metal may be further improved by forming a stable film on the surface of the electrode. Also, if the amount of the electrolyte solution additive for a secondary battery is 5 wt % or less, a side reaction due to the somewhat large amount of the additive may be prevented.

Specifically, the electrolyte solution additive for a secondary battery may be present in an amount of 0.05 wt % to 5 wt %, more preferably in amounts of 0.05 wt % to 4 wt %, 0.1 wt % to 3 wt %, for example, 0.5 wt % to 3 wt % based on the total weight of the non-aqueous electrolyte solution.

(2) Lithium Salt

Any lithium salt typically used in an electrolyte solution for a lithium secondary battery may be used as the lithium salt without limitation, and, for example, the lithium salt may include Li$^+$ as a cation, and may include at least one selected from the group consisting of F$^-$, Cl$^-$, Br$^-$, I$^-$, NO$_3^-$, N(CN)$_2^-$, BF$_4^-$, ClO$_4^-$, B$_{10}$Cl$_{10}^-$, AlCl$_4^-$, AlO$_2^-$, PF$_6^-$, CF$_3$SO$_3$, CH$_3$CO$_2^-$, CF$_3$CO$_2^-$, AsF$_6^-$, SbF$_6^-$, CH$_3$SO$_3^-$, (CF$_3$CF$_2$SO$_2$)$_2$N$^-$, (CF$_3$SO$_2$)$_2$N$^-$, (FSO$_2$)$_2$N$^-$, BF$_2$C$_2$O$_4^-$, BC$_4$O$_8^-$, PF$_4$C$_2$O$_4^-$, PF$_2$C$_4$O$_8^-$, (CF$_3$)$_2$PF$_4^-$, (CF$_3$)$_3$PF$_3^-$, (CF$_3$)$_4$PF$_2^-$, (CF$_3$)$_5$PF$^-$, (CF$_3$)$_6$P$^-$, C$_4$F$_9$SO$_3^-$, CF$_3$CF$_2$SO$_3^-$, CF$_3$CF$_2$ (CF$_3$)$_2$CO$^-$, (CF$_3$SO$_2$)$_2$CH$^-$, CF$_3$ (CF$_2$)$_7$SO$_3$, and SCN$^-$ as an anion.

Specifically, the lithium salt may include a single material selected from the group consisting of LiCl, LiBr, LiI, LiBF$_4$, LiClO$_4$, LiB$_{10}$Cl$_{10}$, LiAlCl$_4$, LiAlO$_4$, LiPF$_6$, LiCF$_3$SO$_3$, LiCH$_3$CO$_2$, LiCF$_3$CO$_2$, LiAsF$_6$, LiSbF$_6$, LiCH$_3$SO$_3$, LiN(SO$_2$F)$_2$ (lithium bis(fluorosulfonyl)imide, LiFSI), LiN(SO$_2$CF$_2$CF$_3$)$_2$ (lithium bis(perfluoroethanesulfonyl)imide, LiBETI), and LiN(SO$_2$CF$_3$)$_2$ (lithium bis(trifluoromethanesulfonyl)imide, LiTFSI) or a mixture of two or more thereof. In addition to them, a lithium salt typically used in an electrolyte solution of a lithium secondary battery may be used without limitation.

The lithium salt may be appropriately changed in a normally usable range, but may be included in a concentration of 0.8 M to 4.0 M, for example, 1.0 M to 3.0 M in the electrolyte solution to obtain an optimum effect of forming a film for preventing corrosion of the surface of the electrode.

In a case in which the concentration of the lithium salt satisfies the above range, low-temperature output characteristics and cycle characteristics during high-temperature storage may be improved by improving mobility of lithium ions, and viscosity of the non-aqueous electrolyte solution may be controlled so that optimum impregnability may be achieved.

(3) Non-Aqueous Organic Solvent

Also, a non-aqueous organic solvent will be described as follows.

Various organic solvents typically used in a non-aqueous electrolyte solution may be used as the non-aqueous organic solvent without limitation, wherein a type of the non-aqueous organic solvent is not limited as long as the non-aqueous organic solvent may minimize decomposition due to an oxidation reaction during charge and discharge of the secondary battery and may exhibit desired characteristics with the additive.

Specifically, the non-aqueous organic solvent may include a cyclic carbonate-based organic solvent, a linear carbonate-based organic solvent, or a mixed organic solvent thereof.

The cyclic carbonate-based organic solvent is a highly viscous organic solvent which well dissociates the lithium salt in a non-aqueous electrolyte solution due to high permittivity, wherein specific examples thereof may be at least one non-aqueous organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and, among them, the cyclic carbonate-based organic solvent may include ethylene carbonate.

The linear carbonate-based organic solvent is an organic solvent having low viscosity and low permittivity, wherein typical examples thereof may be at least one non-aqueous organic solvent selected from the group consisting of dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include ethyl methyl carbonate (EMC).

The cyclic carbonate non-aqueous organic solvent and the linear carbonate non-aqueous organic solvent may be mixed and used as the non-aqueous organic solvent of the present invention, and, in this case, the cyclic carbonate non-aqueous organic solvent and the linear carbonate non-aqueous organic solvent may be used by being mixed in a volume ratio of 10:90 to 50:50, for example, 20:80 to 30:70.

Furthermore, in order to prepare an electrolyte solution having high ionic conductivity, the non-aqueous organic solvent may further include a linear ester-based non-aqueous organic solvent and/or a cyclic ester-based non-aqueous organic solvent with a low melting point and high stability at high temperatures.

As a representative example, the linear ester-based non-aqueous organic solvent may include at least one non-aqueous organic solvent selected from the group consisting of methyl acetate, ethyl acetate, propyl acetate, methyl propionate, ethyl propionate, propyl propionate, and butyl propionate.

Also, the cyclic ester-based non-aqueous organic solvent may include at least one non-aqueous organic solvent selected from the group consisting of γ-butyrolactone, γ-valerolactone, γ-caprolactone, σ-valerolactone, and ε-caprolactone.

A remainder excluding other components excluding the non-aqueous organic solvent in the non-aqueous electrolyte solution of the present invention, for example, the electrolyte solution additive for a secondary battery of the present invention, the lithium salt, and other additives may all be the non-aqueous organic solvent unless otherwise stated.

(4) Other Additives

Also, the non-aqueous electrolyte solution for a lithium secondary battery of the present invention may further include other additives so as to be able to form a more stable film on the surface of the positive electrode due to a synergistic effect with the compound represented by Formula 1.

The other additives may include a compound in which an absolute value of a difference in reduction potential versus lithium between the compound and the compound represented by Formula 1 is in a range of 0.0 V to 2.2 V. That is, due to the difference in the reduction potential between the compound represented by Formula 1 of the present invention and the other additives, thermal stability and ion transfer properties of the film may be further strengthened by changing SEI or cathode electrolyte interphase (CEI) components. With respect to a compound in which the absolute value of the difference in reduction potential versus lithium between the compound and the compound represented by Formula 1 is greater than 2.2 V, since it does not participate in an initial SEI formation reaction by reacting beyond a decomposition reaction region of the solvent, it may cause an increase in volume of the cell during high-temperature storage.

Thus, the other additives of the present invention may include at least one selected from the group consisting of a halogen-unsubstituted or substituted carbonate-based compound, a sultone-based compound, a sulfate-based compound, a phosphate-based or phosphite-based compound, a borate-based compound, a nitrile-based compound, an amine-based compound, a silane-based compound, and a lithium salt-based compound, except for an overcharge inhibitor including a benzene group, such as monofluorobenzene, in which the absolute of the difference in reduction potential versus lithium is greater than 2.2 V, and may more specifically include a halogen-unsubstituted or substituted carbonate-based compound.

Typical examples of the halogen-unsubstituted or substituted carbonate-based compound may be vinylene carbonate (VC), vinylethylene carbonate, or fluoroethylene carbonate (FEC).

The sultone-based compound may be at least one compound selected from the group consisting of 1,3-propane sultone (PS), 1,4-butane sultone, ethane sultone, and 1,3-propene sultone (PRS).

The sulfate-based compound, for example, may be ethylene sulfate (Esa), trimethylene sulfate (TMS), or methyl trimethylene sulfate (MTMS).

The phosphate-based or phosphite-based compound may be at least one compound selected from the group consisting of lithium difluoro(bisoxalato)phosphate, lithium difluorophosphate, tris(trimethylsilyl)phosphite, and tris(2,2,2-trifluoroethyl)phosphate.

The borate-based compound may be tetraphenylborate, lithium oxalyldifluoroborate (LiODFB), or lithium bisoxalatoborate (LiB($C_2O_4$)$_2$; LiBOB).

The nitrile-based compound, for example, may be at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The lithium salt-based compound is a compound different from the lithium salt included in the non-aqueous electrolyte solution, wherein the lithium salt-based compound may include $LiPO_2F_2$ or $LiBF_4$.

Two or more compounds may be mixed and used as the other additives, and the other additives may be present in an amount of 0.01 wt % to 10 wt %, particularly 0.05 wt % to 7 wt %, and preferably 0.1 wt % to 5 wt % based on the total weight of the non-aqueous electrolyte solution.

If the amount of the other additives included is within the above range, an effect of improving low-temperature output characteristics, high-temperature storage characteristics, and high-temperature life characteristics of the secondary battery may be obtained, and a side reaction of the battery due to the excessive amount of the additives may be prevented. Also, that an unreacted material is formed in the electrolyte solution at room temperature or the other additives may be present in the form of precipitates due to insufficient decomposition of the other additives at high temperature may be prevented.

Lithium Secondary Battery

Next, a lithium secondary battery according to the present invention will be described.

The lithium secondary battery according to the present invention includes a positive electrode, a negative electrode, a separator disposed between the positive electrode and the negative electrode, and a non-aqueous electrolyte solution, and, in this case, the non-aqueous electrolyte solution is the non-aqueous electrolyte solution according to the present invention. Since the non-aqueous electrolyte solution has been described above, a description thereof will be omitted and other components will be described below.

(1) Positive Electrode

The positive electrode according to the present invention may include a positive electrode active material layer including a positive electrode active material, and, if necessary, the positive electrode active material layer may further include a conductive agent and/or a binder.

The positive electrode active material is a compound capable of reversibly intercalating and deintercalating lithium, wherein the positive electrode active material may specifically include a lithium composite metal oxide including lithium and at least one metal selected from the group consisting of nickel (Ni), cobalt (Co), manganese (Mn), iron (Fe), and aluminum (Al), and may particularly include a high-nickel (Ni) lithium composite metal oxide in which a Ni content is high at 0.55 or more.

With respect to the lithium composite metal oxide having a high Ni content, despite the advantage of being able to achieve a high-capacity battery, it has a disadvantage in that $Ni^{2+}$ cations are dissolved from the positive electrode into the electrolyte solution, the $Ni^{2+}$ cations react with a passivation film (SEI) of the negative electrode to decompose the SEI, and, as a result, since a portion of the negative electrode active material is exposed to the electrolyte solution to cause a side reaction, capacity and life characteristics are degraded and resistance is increased. Also, with respect to the high-Ni positive electrode active material, the dissolution of the transition metal may be intensified by acceleration of structural collapse of the positive electrode due to high-temperature exposure, and may be accelerated particularly when HF is present in the electrolyte solution.

Thus, in order to solve this problem, the lithium secondary battery of the present invention is characterized in that it employs the non-aqueous electrolyte solution containing the compound represented by Formula 1 as an additive. That is, due to the additive included in the non-aqueous electrolyte solution, stabilization of the film on the surface of the positive electrode may not only be achieved, but also a Lewis acid in the non-aqueous electrolyte solution may be scavenged to prevent degradation of the film and an effect of reducing resistance may be achieved by interaction with the $Ni^{2+}$ cations dissolved into the electrolyte solution to stabilize them. Therefore, degradation of high-temperature durability, high-temperature capacity, and life characteristics of the lithium secondary battery may be prevented.

Typical examples of the lithium composite metal oxide may be $Li(Ni_{0.6}Mn_{0.2}Co_{0.2})O_2$, $Li(Ni_{0.7}Mn_{0.2}Co_{0.1})O_2$, $Li(Ni_{0.8}Mn_{0.1}Co_{0.1})O_2$, $Li[Ni_{0.8}CO_{0.15}Al_{0.05}]O_2$, $Li[Ni_{0.86}Mn_{0.07}Co_{0.05}Al_{0.02}]O_2$, or $Li(Ni_{0.9}Mn_{0.05}Co_{0.05})O_2$.

Also, in addition to the above-described lithium composite metal oxide, the positive electrode active material may further include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$)), lithium-nickel-cobalt-based oxide (e.g., $LiNi_{1-Y1}Co_{Y1}O_2$ (where $0<Y1<1$)), lithium-manganese-cobalt-based oxide (e.g., $LiCO_{1-Y2}Mn_{Y2}O_2$ (where $0<Y2<1$), $LiMn_{2-Z1}Co_{z1}O_4$ (where $0<Z1<2$)), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}CO_{q1}Mn_{r2})O_4$ (where $0<p1<2$, $0<q1<2$, $0<r2<2$, and $p1+q1+r2=2$), or lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<s2<1$, and $p2+q2+r3+s2=1$).

The positive electrode active material may be included in an amount of 80 wt % to 98 wt %, for example, 85 wt % to 98 wt % based on a total weight of the positive electrode active material layer. When the positive electrode active material is present in an amount within the above range, excellent capacity characteristics may be exhibited.

Next, the conductive agent is used to provide conductivity to the electrode, wherein any conductive agent may be used without particular limitation as long as it has suitable electron conductivity without causing adverse chemical changes in the battery. Specific examples of the conductive agent may be a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, and any one thereof or a mixture of two or more thereof may be used.

The conductive agent may be included in an amount of 0.1 wt % to 10 wt %, for example, 0.1 wt % to 5 wt % based on the total weight of the positive electrode active material layer.

Next, the binder improves the adhesion between positive electrode active material particles and the adhesion between the positive electrode active material and a current collector.

As an example of the binder, any one of a fluorine resin-based binder including polyvinylidene fluoride (PVDF) or polytetrafluoroethylene (PTFE); a rubber-based binder including a styrene butadiene rubber (SBR), an acrylonitrile-butadiene rubber, or a styrene-isoprene rubber; a cellulose-based binder including carboxymethylcellulose (CMC), starch, hydroxypropylcellulose, or regenerated cellulose; a polyalcohol-based binder including polyvinyl alcohol; a polyolefin-based binder including polyethylene or polypropylene; a polyimide-based binder; a polyester-based binder; and a silane-based binder or a mixture of two or more thereof may be used.

The binder may be included in an amount of 0.1 wt % to 15 wt %, for example, 0.1 wt % to 10 wt % based on the total weight of the positive electrode active material layer.

The positive electrode of the present invention as described above may be prepared by a method of preparing a positive electrode which is known in the art. For example, the positive electrode may be prepared by a method in which a positive electrode collector is coated with a positive electrode slurry, which is prepared by dissolving or dispersing the positive electrode active material, the binder, and/or the conductive agent in a solvent, dried, and then rolled to form an active material layer, or a method in which the positive electrode active material layer is cast on a separate support and a film separated from the support is then laminated on the positive electrode collector.

The positive electrode collector is not particularly limited as long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used. Also, the positive electrode collector may typically have a thickness of 3 µm to 500 µm, and microscopic irregularities may be formed on the surface of the collector to improve the adhesion of the positive electrode material. The positive electrode collector, for example, may be used in various shapes such as that of a film, a sheet, a foil, a net, a porous body, a foam body, a non-woven fabric body, and the like.

The solvent may be a solvent normally used in the art, and may include dimethyl sulfoxide (DMSO), isopropyl alcohol, N-methylpyrrolidone (NMP), acetone, or water, and any one thereof or a mixture of two or more thereof may be used. An amount of the solvent used may be sufficient if a positive electrode material mixture may be adjusted to have appropriate viscosity in consideration of a coating thickness of the positive electrode material mixture, manufacturing yield, and workability, and is not particularly limited.

(2) Negative Electrode

Next, a negative electrode will be described.

The negative electrode according to the present invention includes a negative electrode active material layer including a negative electrode active material, and the negative electrode active material layer may further include a conductive agent and/or a binder, if necessary.

Various negative electrode active materials used in the art, for example, a carbon-based negative electrode active material, a silicon-based negative electrode active material, or a mixture thereof may be used as the negative electrode active material.

According to an embodiment, the negative electrode active material may include a carbon-based negative electrode active material, and, as the carbon-based negative electrode active material, various carbon-based negative electrode active materials used in the art, for example, a graphite-based materials such as natural graphite, artificial graphite, and Kish graphite; pyrolytic carbon, mesophase pitch based carbon fiber, meso-carbon microbeads, mesophase pitches, high-temperature sintered carbon such as petroleum or coal tar pitch derived cokes, soft carbon, and hard carbon may be used. A shape of the carbon-based negative electrode active material is not particularly limited, and materials of various shapes, such as an irregular shape, planar shape, flaky shape, spherical shape, or fibrous shape, may be used.

Preferably, the carbon-based negative electrode active material may include at least one of natural graphite and artificial graphite. More preferably, the carbon-based negative electrode active material may include natural graphite and artificial graphite. In a case in which the natural graphite and the artificial graphite are used together, adhesion with the current collector may be increased to suppress exfoliation of the active material.

According to another embodiment, the negative electrode active material may include a carbon-based negative electrode active material and a silicon-based negative electrode active material.

Specific examples of the carbon-based negative electrode active material are the same as described above.

The silicon-based negative electrode active material, for example, may include at least one selected from the group consisting of metallic silicon (Si), silicon oxide ($SiO_x$, where $0<x<2$), silicon carbide (SiC), and a Si—Y alloy (where Y is an element selected from the group consisting of alkali metal, alkaline earth metal, a Group 13 element, a Group 14 element, transition metal, a rare earth element, and a combination thereof, and is not Si). The element Y may be selected from the group consisting of Mg, calcium (Ca), strontium (Sr), barium (Ba), radium (Ra), scandium (Sc), yttrium (Y), Ti, zirconium (Zr), hafnium (Hf), rutherfordium (Rf), V, niobium (Nb), Ta, dubnium (db), Cr, Mo, tungsten (W), seaborgium (Sg), technetium (Tc), rhenium (Re), bohrium (Bh), Fe, lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), Al, gallium (Ga), tin (Sn), indium (In), germanium (Ge), phosphorus (P), arsenic (As), antimony (Sb), bismuth (Bi), sulfur (S), selenium (Se), tellurium (Te), polonium (Po), and a combination thereof.

Since the silicon-based negative electrode active material has higher capacity characteristics than the carbon-based negative electrode active material, better capacity characteristics may be obtained when the silicon-based negative electrode active material is further included. However, with respect to a negative electrode including the silicon-based negative electrode active material, it contains more oxygen (O)-rich (O-rich) components in the SEI than a graphite negative electrode, and the SEI containing the O-rich components tends to be more easily decomposed when a Lewis acid, such as HF or $PF_5$, is present in the electrolyte solution. Thus, with respect to the negative electrode including the silicon-based negative electrode active material, there is a need to suppress the formation of the Lewis acid, such as HF and $PF_5$, in the electrolyte solution or remove (or scavenge) the formed Lewis acid in order to stably maintain the SEI. Since the non-aqueous electrolyte solution according to the present invention includes the electrolyte solution additive capable of forming a stable film on the positive electrode and the negative electrode, it may effectively suppress the decomposition of the SEI when the negative electrode including the silicon-based negative electrode active material is used.

A mixing ratio of the silicon-based negative electrode active material to the carbon-based negative electrode active material may be in a range of 3:97 to 99:1, for example, 5:95 to 15:85, as a weight ratio. In a case in which the mixing ratio of the silicon-based negative electrode active material to the carbon-based negative electrode active material satisfies the above range, since a volume expansion of the silicon-based negative electrode active material is suppressed while capacity characteristics are improved, excellent cycle performance may be secured.

The negative electrode active material may be included in an amount of 80 wt % to 99 wt % based on a total weight of the negative electrode active material layer. In a case in which the amount of the negative electrode active material satisfies the above range, excellent capacity characteristics and electrochemical properties may be obtained.

Next, the conductive agent is a component for further improving conductivity of the negative electrode active material, wherein the conductive agent may be added in an amount of 10 wt % or less, for example, 5 wt % or less based on the total weight of the negative electrode active material layer. Any conductive agent may be used without particular limitation so long as it has conductivity without causing adverse chemical changes in the battery, and, for example, a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The binder is a component that assists in the binding between the conductive agent, the active material, and the current collector, wherein the binder is commonly added in an amount of 0.1 wt % to 10 wt % based on the total weight of the negative electrode active material layer. Examples of the binder may be a fluorine resin-based binder including polyvinylidene fluoride (PVDF) or polytetrafluoroethylene (PTFE); a rubber-based binder including a styrene butadiene rubber (SBR), an acrylonitrile-butadiene rubber, or a styrene-isoprene rubber; a cellulose-based binder including carboxymethylcellulose (CMC), starch, hydroxypropylcellulose, or regenerated cellulose; a polyalcohol-based binder including polyvinyl alcohol; a polyolefin-based binder including polyethylene or polypropylene; a polyimide-based binder; a polyester-based binder; and a silane-based binder.

The binder may be included in an amount of 0.1 wt % to 15 wt %, for example, 0.1 wt % to 10 wt % based on the total weight of the negative electrode active material layer.

The negative electrode may be prepared by a method of preparing a negative electrode which is known in the art. For example, the negative electrode may be prepared by a method in which a negative electrode collector is coated with a negative electrode slurry, which is prepared by dissolving or dispersing the negative electrode active material as well as optionally the binder and the conductive agent in a solvent, rolled and dried to form a negative electrode active material layer, or may be prepared by casting the negative electrode active material layer on a separate support and then laminating a film separated from the support on the negative electrode collector.

The negative electrode collector is not particularly limited as long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, or an aluminum-cadmium alloy may be used. Also, the negative electrode collector may typically have a thickness of 3 μm to 500 μm, and, similar to the positive electrode collector, microscopic irregularities may be formed on the surface of the collector to improve the adhesion of the negative electrode active material. The negative electrode collector, for example, may be used in various shapes such as that of a film, a sheet, a foil, a net, a porous body, a foam body, a non-woven fabric body, and the like.

The solvent may be a solvent normally used in the art, and may include dimethyl sulfoxide (DMSO), isopropyl alcohol, N-methylpyrrolidone (NMP), acetone, or water, and any one thereof or a mixture of two or more thereof may be used. An amount of the solvent used may be sufficient if the negative electrode slurry may be adjusted to have appropriate viscosity in consideration of a coating thickness of a negative electrode material mixture, manufacturing yield, and workability, and is not particularly limited.

(3) Separator

The lithium secondary battery according to the present invention includes a separator between the positive electrode and the negative electrode.

The separator separates the negative electrode and the positive electrode and provides a movement path of lithium ions, wherein any separator may be used without particular limitation as long as it is typically used as a separator in a lithium secondary battery, and particularly, a separator having high moisture-retention ability for an electrolyte solution as well as low resistance to the transfer of ions of the lithium salt may be used.

Specifically, a porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, or a laminated structure having two or more layers thereof may be used. Also, a typical porous nonwoven fabric, for example, a nonwoven fabric formed of high melting point glass fibers or polyethylene terephthalate fibers may be used. Furthermore, a coated separator including a ceramic component or a polymer material may be used to secure heat resistance or mechanical strength, and the separator having a single layer or multilayer structure may be optionally used.

The lithium secondary battery according to the present invention as described above may be suitably used in portable devices, such as mobile phones, notebook computers, and digital cameras, and electric cars such as a hybrid electric vehicle (HEV).

Thus, according to another embodiment of the present invention, a battery module including the lithium secondary battery as a unit cell and a battery pack including the battery module are provided.

The battery module or the battery pack may be used as a power source of at least one medium and large sized device of a power tool; electric cars including an electric vehicle (EV), a hybrid electric vehicle (HEV), and a plug-in hybrid electric vehicle (PHEV); or a power storage system.

A shape of the lithium secondary battery of the present invention is not particularly limited, but a cylindrical type using a can, a prismatic type, a pouch type, or a coin type may be used.

The lithium secondary battery according to the present invention may not only be used in a battery cell that is used as a power source of a small device, but may also be used as a unit cell in a medium and large sized battery module including a plurality of battery cells.

Hereinafter, the present invention will be described in detail, according to specific examples.

EXAMPLES

Example 1

(Non-Aqueous Electrolyte Solution Preparation)

$LiPF_6$ was dissolved in 99 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 0.5 g of the compound represented by Formula 1A-1 as an additive and 0.5 g of vinylene carbonate (absolute value of difference in reduction potential versus lithium between the vinylene carbonate and the compound of Formula 1A-1: 0.7 V) as other additives (see Table 1 below).

(Positive Electrode Preparation)

A lithium nickel-manganese-aluminum oxide (Li$(Ni_{0.86}Mn_{0.07}Co_{0.05}Al_{0.02})O_2$) as positive electrode active material particles, carbon black as a conductive agent, and polyvinylidene fluoride (PVDF), as a binder, were added to N-methyl-2-pyrrolidone (NMP), as a solvent, at a weight ratio of 90:5:5 to prepare a positive electrode active material slurry (solid content 48 wt %). A 100 μm thick positive electrode collector (Al thin film) was coated with the positive electrode active material slurry, dried, and then roll-pressed to prepare a positive electrode.

(Negative Electrode Preparation)

A negative electrode active material (artificial graphite: SiO=94.5:5.5 weight ratio), PVDF as a binder, and carbon black, as a conductive agent, were added to NMP, as a solvent, at a weight ratio of 95:2:3 to prepare a negative electrode active material slurry (solid content: 70 wt %). A 90 μm thick negative electrode collector (Cu thin film) was coated with the negative electrode active material slurry, dried, and then roll-pressed to prepare a negative electrode.

(Secondary Battery Preparation)

After an electrode assembly was prepared by a conventional method of sequentially stacking a polyethylene porous film with the positive electrode and negative electrode prepared by the above-described methods, the electrode assembly was put in a pouch-type secondary battery case, and the above-prepared non-aqueous electrolyte solution was injected thereinto to prepare a lithium secondary battery.

Example 2

A lithium secondary battery was prepared in the same manner as in Example 1 except that $LiPF_6$ was dissolved in 98.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 1.0 g of the compound represented by Formula 1A-1 as an additive and 0.5 g of vinylene carbonate (absolute value of difference in reduction potential versus lithium between the vinylene carbonate and the compound of Formula 1A-1: 0.7 V) as other additives (see Table 1 below).

Example 3

A lithium secondary battery was prepared in the same manner as in Example 1 except that $LiPF_6$ was dissolved in 96.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 3.0 g of the compound represented by Formula 1A-1 as an additive and 0.5 g of vinylene carbonate (absolute value of difference in reduction potential versus lithium between the vinylene carbonate and the compound of Formula 1A-1: 0.7 V) as other additives (see Table 1 below).

Example 4

A lithium secondary battery was prepared in the same manner as in Example 1 except that $LiPF_6$ was dissolved in 94.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 5.0 g of the compound represented by Formula 1A-1 as an additive and 0.5 g of vinylene carbonate (absolute value of difference in reduction potential versus lithium between the vinylene carbonate and the compound of Formula 1A-1: 0.7 V) as other additives (see Table 1 below).

Example 5

A lithium secondary battery was prepared in the same manner as in Example 1 except that $LiPF_6$ was dissolved in 99.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 0.5 g of the compound represented by Formula 1A-1 as an additive (see Table 1 below).

Example 6

A lithium secondary battery was prepared in the same manner as in Example 1 except that a non-aqueous electrolyte solution was prepared by adding the compound represented by Formula 1B-1, instead of the compound represented by Formula 1A-1 (see Table 1 below).

Example 7

A lithium secondary battery was prepared in the same manner as in Example 1 except that $LiPF_6$ was dissolved in 99 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 0.5 g of the compound represented by Formula 1A-1 as an additive and 0.5 g of monofluorobenzene (absolute value of difference in reduction potential versus lithium between the fluorobenzene and the compound of Formula 1A-1: 2.2 V) as other additives (see Table 1 below).

Comparative Example 1

A lithium secondary battery was prepared in the same manner as in Example 1 except that, after $LiPF_6$ was dissolved in 99.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, the electrolyte solution additive of the present invention was not included, and a non-aqueous electrolyte solution was prepared by adding 0.5 g of vinylene carbonate as other additives (see Table 1 below).

Comparative Example 2

A lithium secondary battery was prepared in the same manner as in Example 1 except that $LiPF_6$ was dissolved in 99.5 g of a non-aqueous organic solvent, in which ethylene carbonate (EC) and ethyl methyl carbonate (EMC) were mixed in a volume ratio of 30:70, such that a concentration of the $LiPF_6$ was 1.0 M, and a non-aqueous electrolyte solution was prepared by adding 0.5 g of a compound represented by the following Formula 3 as an additive (see Table 1 below).

With respect to a compound, in which a phenyl group is bonded to a nitrogen element, such as a compound represented by the following Formula 3, even if it is a zwitterionic compound of an imidazole structure having a structure similar to that of the compound of the present invention, a nitrophenyl-based SEI is formed, wherein, since the SEI has a greater binding energy with lithium ions than a sulfonate-based SEI, lithium ion transfer properties may be deteriorated, and thus, an effect of improving battery durability, such as initial resistance increase and capacity retention decrease, may be insignificant.

[Formula 3]

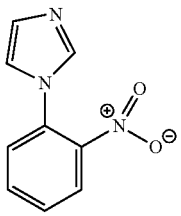

Such compound is a zwitterionic compound in an imidazole structure in which the structure is similar to the compound of the present invention. However, because a phenyl group is bonded to a nitrogen element, a nitrophenyl-based SEI is formed. Such nitrophenyl-based SEI has a greater binding energy with lithium ions than a sulfonate-based SEI, and lithium ion transfer properties may be deteriorated, and thus, an effect of improving battery durability, such as initial resistance increase and capacity retention decrease may be insignificant.

Comparative Example 3

A lithium secondary battery was prepared in the same manner as in Example 1 except that LiPF$_6$ was dissolved in 99 g of a non-aqueous organic solvent, in which ethylene carbonate (EC) and ethyl methyl carbonate (EMC) were mixed in a volume ratio of 30:70, such that a concentration of the LiPF$_6$ was 1.0 M, and a non-aqueous electrolyte solution was prepared by adding 0.5 g of the compound represented by Formula 3 as an additive and 0.5 g of vinylene carbonate (absolute value of difference in reduction potential versus lithium between the vinylene carbonate and the compound of Formula 3: 0.7 V) as other additives (see Table 1 below).

Comparative Example 4

A lithium secondary battery was prepared in the same manner as in Example 1 except that LiPF$_6$ was dissolved in 94.5 g of a non-aqueous organic solvent, in which ethylene carbonate (EC) and ethyl methyl carbonate (EMC) were mixed in a volume ratio of 30:70, such that a concentration of the LiPF$_6$ was 1.0 M, and a non-aqueous electrolyte solution was prepared by adding 5.0 g of the compound represented by Formula 3 as an additive and 0.5 g of vinylene carbonate (absolute value of difference in reduction potential versus lithium between the vinylene carbonate and the compound of Formula 3: 0.7 V) as other additives (see Table 1 below).

Comparative Example 5

A lithium secondary battery was prepared in the same manner as in Example 1 except that a non-aqueous electrolyte solution was prepared by adding a compound represented by the following Formula 4, instead of the compound represented by Formula 1A-1 (see Table 1 below).

[Formula 4]

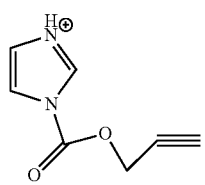

TABLE 1

| | Electrolyte solution additive of the present invention | | Other additives | | Difference in absolute values of reduction potential between the electrolyte solution additive of the present invention and the other additives (V) |
|---|---|---|---|---|---|
| | Formula | Amount (g) | Type | Amount (g) | |
| Example 1 | 1A-1 | 0.5 | VC | 0.5 | 0.7 |
| Example 2 | 1A-1 | 1.0 | VC | 0.5 | 0.7 |
| Example 3 | 1A-1 | 3.0 | VC | 0.5 | 0.7 |
| Example 4 | 1A-1 | 5.0 | VC | 0.5 | 0.7 |
| Example 5 | 1A-1 | 0.5 | — | — | — |
| Example 6 | 1B-1 | 0.5 | VC | 0.5 | 0.7 |
| Example 7 | 1A-1 | 0.5 | FB | 0.5 | 2.2 V |
| Comparative Example 1 | — | — | VC | 0.5 | — |
| Comparative Example 2 | 3 | 0.5 | — | — | — |
| Comparative Example 3 | 3 | 0.5 | VC | 0.5 | 0.7 |
| Comparative Example 4 | 3 | 5.0 | VC | 0.5 | 0.7 |
| Comparative Example 5 | 4 | 0.5 | VC | 0.5 | 0.7 |

In Table 1, the abbreviations of compounds are as follows.
VC: vinylene carbonate
FB: monofluorobenzene

EXPERIMENTAL EXAMPLES

Experimental Example 1: Initial Resistance Evaluation

After each of the lithium secondary batteries prepared in Examples 1 to 7 and the lithium secondary batteries prepared in Comparative Examples 1 to 4 was charged at 0.33 C rate to 4.2 V under a constant current/constant voltage condition at room temperature (25° C.), each lithium secondary battery was discharged to a DOD (depth of discharge) of 50% to adjust a state of charge (SOC) to 50% and then discharged at 2.5 C rate for 10 seconds, and initial resistance was measured using PNE-0506 charge/discharge equipment (manufacturer: PNE solution). The results thereof are listed in Table 2 below.

TABLE 2

| | Initial resistance |
|---|---|
| Example 1 | 5.31 |
| Example 2 | 5.47 |
| Example 3 | 5.72 |
| Example 4 | 6.01 |
| Example 5 | 5.11 |
| Example 6 | 5.57 |
| Example 7 | 5.32 |
| Comparative Example 1 | 6.07 |
| Comparative Example 2 | 6.24 |
| Comparative Example 3 | 6.28 |
| Comparative Example 4 | 7.24 |
| Comparative Example 5 | 6.75 |

Referring to Table 2, it may be understood that initial resistances of the secondary batteries of Examples 1 to 7 of the present invention were about 6.01 mohm or less.

In contrast, with respect to the secondary batteries of Comparative Examples 2 to 4 which included the non-aqueous electrolyte solution containing the compound represented by Formula 3, a zwitterionic compound having an imidazole structure, it may be understood that initial resistances were all increased in comparison to those of the secondary batteries of the examples.

Also, with respect to the secondary battery of Comparative Example 5 which included the non-aqueous electrolyte solution containing the compound represented by Formula 4, it may be understood that initial resistance was increased in comparison to those of the secondary batteries of the examples.

Experimental Example 2. High-Temperature Cycle Characteristics Evaluation

That each of the lithium secondary batteries prepared in Examples 1 to 7 and Comparative Examples 1 to 5 was charged at 0.33 C rate to 4.2 V under a constant current/constant voltage condition at 45° C. and then discharged at 0.33 C rate under a constant current condition to 3 V was defined as one cycle and capacity retention (%) and resistance increase rate (%) were measured after 100 cycles of charge and discharge were performed. The capacity retention (%) was calculated according to Equation 1 below, and the resistance increase rate (%) was calculated according to Equation 2 below. Measurement results are listed in Table 3 below.

Capacity retention (%)=(discharge capacity after 100 cycles/discharge capacity after 1 cycle)×100     [Equation 1]

Resistance increase rate (%)={(resistance after 100 cycles−resistance after 1 cycle)/resistance after 1 cycle}×100     [Equation 2]

TABLE 3

|  | Capacity retention (%) after 100 cycles | Resistance increase rate (%) after 100 cycles |
| --- | --- | --- |
| Example 1 | 98.9 | 1.10 |
| Example 2 | 99.0 | 1.02 |
| Example 3 | 99.2 | 0.94 |
| Example 4 | 98.0 | 1.32 |
| Example 5 | 98.6 | 1.11 |
| Example 6 | 95.9 | 2.67 |
| Example 7 | 98.7 | 1.11 |
| Comparative Example 1 | 78.2 | 34.5 |
| Comparative Example 2 | 85.2 | 15.4 |
| Comparative Example 3 | 86.4 | 13.4 |
| Comparative Example 4 | 87.2 | 12.1 |
| Comparative Example 5 | 84.5 | 16.2 |

Referring to Table 3, it may be understood that capacity retentions (%) after 100 cycles of the secondary batteries of Examples 1 to 7 of the present invention were about 95.9% or more, and resistance increase rates (%) were about 2.67% or less.

In contrast, with respect to the secondary battery of Comparative Example 1 including the non-aqueous electrolyte solution without the compound of Formula 1A-1, the secondary batteries of Comparative Examples 2 to 4 which included the non-aqueous electrolyte solutions containing the compound of Formula 3 instead of the compound of Formula 1A-1, and the secondary battery of Comparative Example 5 which included the non-aqueous electrolyte solution containing the compound of Formula 4, it may be understood that capacity retentions (%) and resistance increase rates (%) after 100 cycles were significantly degraded in comparison to those of the secondary batteries of Examples 1 to 7.

On the other hand, in the case of a secondary battery of Example 7 which includes a monofluorobenzene instead of a vinylene carbonate as an other additive, the capacity retention (%) after 100 cycles is decreased by a relatively small amount, and the resistance increase rate (%) is increased by a relatively small amount, compared to the secondary battery of Example 1. Such difference may be further increased as the cycle is repeated.

Experimental Example 3. Characteristics Evaluation after High-Temperature Storage (1)

After each of the lithium secondary batteries prepared in Examples 1 to 7 and the lithium secondary batteries prepared in Comparative Examples 1 to 5 was fully charged (state of charge (SOC) of 100%) at 0.33 C rate to 4.2 V and a cut-off current of 50 mA under a constant current/constant voltage condition at room temperature (25° C.) and discharged at 0.33 C rate under a constant current condition to 3 V, discharge capacity before high-temperature storage was measured using PNE-0506 charge/discharge equipment (manufacturer: PNE solution).

Then, after each lithium secondary battery was stored at 60° C. for 2 weeks, capacity after high-temperature storage was measured for each lithium secondary battery, and a high-temperature capacity retention (%) was then calculated using Equation 3 below. The results thereof are listed in Table 4 below.

Capacity retention (%)=(discharge capacity after 2 weeks high-temperature storage/discharge capacity before high-temperature storage)×100     [Equation 3]

Experimental Example 4. Characteristics Evaluation after High-Temperature Storage (2)

After each of the lithium secondary batteries prepared in Examples 1 to 7 and the lithium secondary batteries prepared in Comparative Examples 1 to 5 was charged at 0.33 C rate to 4.2 V under a constant current/constant voltage condition at room temperature (25° C.), each lithium secondary battery was discharged to a DOD (depth of discharge) of 50% to adjust a SOC to 50% and then discharged at 2.5 C rate for 10 seconds, and initial resistance was measured using PNE-0506 charge/discharge equipment (manufacturer: PNE solution).

Then, after each lithium secondary battery was stored at 60° C. for 2 weeks, a resistance value of each lithium secondary battery was measured, and a resistance increase rate (%) was calculated using Equation 4 below. The results thereof are listed in Table 4 below.

Resistance increase rate (%)={(resistance value after 2 weeks high-temperature storage−resistance value before high-temperature storage)/resistance value before high-temperature storage}×100     [Equation 4]

TABLE 4

|  | Discharge capacity after high-temperature storage (%) | Resistance increase rate after high-temperature storage (%) |
| --- | --- | --- |
| Example 1 | 97.9 | 3.2 |
| Example 2 | 98.1 | 3.0 |

TABLE 4-continued

|  | Discharge capacity after high-temperature storage (%) | Resistance increase rate after high-temperature storage (%) |
|---|---|---|
| Example 3 | 98.2 | 2.6 |
| Example 4 | 95.4 | 5.2 |
| Example 5 | 97.4 | 3.5 |
| Example 6 | 94.1 | 6.3 |
| Example 7 | 97.6 | 3.3 |
| Comparative Example 1 | 76.4 | 32.4 |
| Comparative Example 2 | 85.4 | 6.9 |
| Comparative Example 3 | 87.4 | 6.5 |
| Comparative Example 4 | 81.1 | 8.9 |
| Comparative Example 5 | 83.4 | 7.5 |

Referring to Table 4, it may be understood that capacity retentions (%) after 2 weeks storage at high temperature of the secondary batteries of Examples 1 to 7 of the present invention were about 94.1% or more, and resistance increase rates (%) were about 6.3% or less.

In contrast, with respect to the secondary battery of Comparative Example 1 including the non-aqueous electrolyte solution without the compound of Formula 1A-1, the secondary batteries of Comparative Examples 2 to 4 which included the non-aqueous electrolyte solutions containing the compound of Formula 3 instead of the compound of Formula 1A-1, and the secondary battery of Comparative Example 5 which included the non-aqueous electrolyte solution containing the compound of Formula 4, it may be understood that capacity retentions (%) and resistance increase rates (%) after high-temperature storage were significantly degraded in comparison to those of the secondary batteries of Examples 1 to 7.

On the other hand, in the case of the secondary battery of Example 7 which includes the monofluorobenzene instead of vinylene carbonate as an other additive, after 2 weeks storage at high temperature, the capacity retention (%) is decreased by a relatively small amount, and the resistance increase rate (%) is increased by a relatively small amount, compared to the secondary battery of Example 1. Such difference may be further increased as the storing time at high temperature becomes longer.

Experimental Example 5. Volume Increase Rate Evaluation after High-Temperature Storage After each of the lithium secondary batteries prepared in Examples 1 to 7 and the lithium secondary batteries prepared in Comparative Examples 1 to 5 was charged at 0.33 C rate to 4.2 V under a constant current/constant voltage condition at room temperature (25° C.), each lithium secondary battery was discharged to a DOD (depth of discharge) of 50% to adjust a SOC to 50% and discharged at 2.5 C rate for 10 seconds, and an initial thickness was then measured.

Then, after each lithium secondary battery was stored at 60° C. for 2 weeks, a thickness (volume increase rate (%)) after high-temperature storage of each lithium secondary battery was measured, and the results thereof are listed in Table 5 below.

TABLE 5

|  | Volume increase rate (%) |
|---|---|
| Example 1 | 4.5 |
| Example 2 | 4.2 |
| Example 3 | 3.4 |
| Example 4 | 3.2 |
| Example 5 | 5.9 |
| Example 6 | 6.5 |
| Example 7 | 5.7 |
| Comparative Example 1 | 25.4 |
| Comparative Example 2 | 7.9 |
| Comparative Example 3 | 7.2 |
| Comparative Example 4 | 7.0 |
| Comparative Example 5 | 8.5 |

Referring to Table 5, it may be understood that volume increase rates (%) after high-temperature storage of the secondary batteries of Examples 1 to 7 of the present invention were about 6.5% or less.

In contrast, with respect to the secondary battery of Comparative Example 1 including the non-aqueous electrolyte solution without the compound of Formula 1A-1, the secondary batteries of Comparative Examples 2 to 4 which included the non-aqueous electrolyte solutions containing the compound of Formula 3 instead of the compound of Formula 1A-1, and the secondary battery of Comparative Example 5 which included the non-aqueous electrolyte solution containing the compound of Formula 4, it may be understood that volume increase rates (%) after high-temperature storage were significantly increased in comparison to those of the secondary batteries of Examples 1 to 7.

With respect to the secondary battery of Example 7 which included the non-aqueous electrolyte solution containing monoflurobenzene (FB) instead of vinylene carbonate as an other additive, a volume increase rates (%) after high-temperature storage was about 5.7%, wherein it may be understood that the volume increase rates (%) after high-temperature storage was increased in comparison to that of the secondary battery of Example 1.

The compound represented by Formula 1, which is included as the non-aqueous electrolyte solution additive of the present invention, is a compound with a zwitterionic structure, as a neutral molecule having anionic and cationic moieties in one molecular structure, wherein it may further improve the ionic conductivity of the non-aqueous electrolyte solution by the zwitterionic structure. Particularly, with respect to the compound represented by Formula 1, since a nitrogen atom of the cationic moiety in the molecular structure acts as a Lewis base, it may effectively scavenge a Lewis acid generated as the decomposition product of the lithium salt. Also, a sulfate group ($-SO_4$), as the anionic moiety of the compound represented by Formula 1, may form a stable film on the surface of the positive electrode or negative electrode.

Thus, since the non-aqueous electrolyte solution for a lithium secondary battery of the present invention forms the stable film on the surface of the positive electrode or negative electrode by including the compound represented by Formula 1 as the additive, it may effectively suppress the dissolution of the transition metal from the positive electrode and may simultaneously scavenge by-products, which are generated by the thermal decomposition of the lithium salt, to reduce the degradation of the solid electrolyte interphase (SEI), and thus, an increase in initial resistance may be suppressed and a lithium secondary battery having improved high-temperature durability, such as high-temperature storage characteristics and high-temperature cycle characteristics, may be achieved.

What is claimed is:

1. A non-aqueous electrolyte solution for a lithium secondary battery, the non-aqueous electrolyte solution comprising:
an electrolyte solution additive comprising a compound represented by Formula 1:

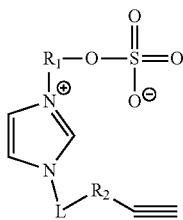

[Formula 1]

wherein, in Formula 1,
$R_1$ and $R_2$ are each independently an unsubstituted or substituted alkylene group having 1 to 5 carbon atoms, and
L is a direct bond, —O—, —COO—, —RO—, or —R'COO—,
wherein R and R' are each independently an alkylene group having 1 to 10 carbon atoms.

2. The non-aqueous electrolyte solution of claim 1, wherein $R_1$ and $R_2$ are each independently an unsubstituted or substituted alkylene group having 1 to 3 carbon atoms, and
L is —O—, —COO—, or —R'COO—, wherein R' is an alkylene group having 1 to 5 carbon atoms.

3. The non-aqueous electrolyte solution of claim 1, wherein L is —O— or —COO—.

4. The non-aqueous electrolyte solution of claim 1, wherein the compound represented by Formula 1 is at least one selected from compounds represented by Formula 1A or Formula 1B:

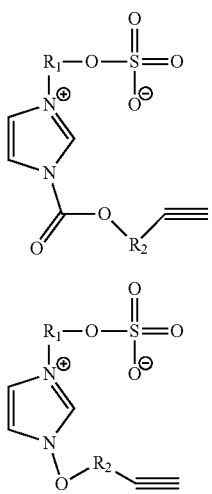

[Formula 1A]

[Formula 1B]

wherein, in Formula 1A or 1B,
$R_1$ and $R_2$ are each independently an unsubstituted or substituted alkylene group having 1 to 5 carbon atoms.

5. The non-aqueous electrolyte solution of claim 1, wherein the compound represented by Formula 1 is at least one selected from compounds represented by Formula 1A-1 or Formula 1B-1:

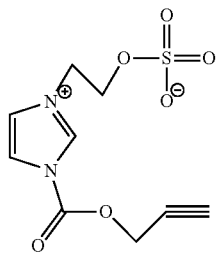

[Formula 1A-1]

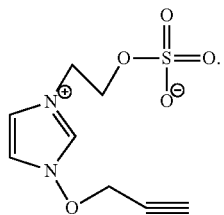

[Formula 1B-1]

6. The non-aqueous electrolyte solution of claim 1, wherein the electrolyte solution additive is present in an amount of 0.05 wt % to 5 wt % based on a total weight of the non-aqueous electrolyte solution.

7. The non-aqueous electrolyte solution of claim 1, further comprising a lithium salt and a non-aqueous organic solvent.

8. The non-aqueous electrolyte solution of claim 1, further comprising other additives in which an absolute value of a difference in reduction potential versus lithium between the other additives and the compound represented by Formula 1 is in a range of 0.0 V to 2.2 V.

9. A lithium secondary battery, comprising:
a positive electrode including a positive electrode active material;
a negative electrode including a negative electrode active material;
a separator disposed between the negative electrode and the positive electrode; and
the non-aqueous electrolyte solution of claim 1.

10. An electrolyte solution additive for a secondary battery, the electrolyte solution additive comprising a compound represented by Formula 1:

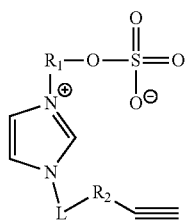

[Formula 1]

wherein, in Formula 1,
$R_1$ and $R_2$ are each independently an unsubstituted or substituted alkylene group having 1 to 5 carbon atoms, and
L is a direct bond, —O—, —COO—, —RO—, or —R'COO—,
wherein R and R' are each independently an alkylene group having 1 to 10 carbon atoms.

* * * * *